United States Patent [19]

Cheminal et al.

[11] Patent Number: 4,579,976

[45] Date of Patent: Apr. 1, 1986

[54] CATALYTIC PROCESS FOR THE PREPARATION OF TRIFLUOROACETALDEHYDE

[75] Inventors: Bernard Cheminal, Lyons; Henri Mathais, Saint Didier au Mont D'or, both of France

[73] Assignee: Atochem, Courbevoie, France

[21] Appl. No.: 679,196

[22] Filed: Dec. 7, 1984

[30] Foreign Application Priority Data

Dec. 13, 1983 [FR] France .............................. 83 19914

[51] Int. Cl.$^4$ ............................................ C07C 45/63
[52] U.S. Cl. .................................. 568/466; 568/458; 568/490
[58] Field of Search .................... 568/458, 490, 466

[56] References Cited

U.S. PATENT DOCUMENTS

| | | | |
|---|---|---|---|
| 3,017,436 | 1/1962 | Hamilton | 568/466 |
| 3,787,489 | 1/1974 | Antonini et al. | 568/407 |
| 3,801,645 | 4/1974 | Dalman | 568/458 |
| 3,803,241 | 4/1974 | Stolkin et al. | 568/466 |

FOREIGN PATENT DOCUMENTS

| | | | |
|---|---|---|---|
| 2221844 | 11/1972 | Fed. Rep. of Germany | 568/466 |
| 1452159 | 10/1966 | France | 568/466 |
| 1372549 | 2/1967 | France | 568/466 |
| 2034536 | 11/1970 | France | 568/466 |

*Primary Examiner*—Werren B. Lone
*Attorney, Agent, or Firm*—Beveridge, DeGrandi & Weilacher

[57] ABSTRACT

There is disclosed a continuous catalytic process for the preparation of trifluoroacetaldehyde through fluorination in the gaseous phase of trichloroacetaldehyde in a single reaction zone at a temperature between 230° C. and 260° C., on a catalyst comprising a gamma alumina impregnated by $Cr_2O_3$ in an amount of 1.5 to 4 atoms of chromium per liter of alumina and activated at a temperature between 300° C. and 400° C. by a mixture of hydrofluoric acid and 1,1,2-trichloro-1,2,2-trifluoroethane.

8 Claims, No Drawings

CATALYTIC PROCESS FOR THE PREPARATION OF TRIFLUOROACETALDEHYDE

The present invention relates to a continuous catalytic process for fluorination in the gaseous phase, by anhydrous hydrofluoric acid, of trichloracetaldehyde (chloral) into trifluoroacetaldehyde (fluoral).

The preparation, through the route defined hereinabove, of fluoral, as well as, moreover, of perfluorinated functional components in general from corresponding perchlorinated compounds, is very difficult to carry out.

The difficulties encountered when utilizing the known processes are set out in French Pat. No. 2,135,474: "The state of the art shows that it is difficult to obtain simultaneously a complete perfluorination of the perchlorinated compounds in a single passage of the reactants in the vapor phase fluorination zone, a suitable yield and a minimal loss of useful matter due to the parasitory reactions of decomposition into non-utilizable compounds".

British Pat. No. 1,036,870 shows that, in conditions considered preferential, i.e. low temperature, for the fluorination of the chloral into fluoral on a pure gel catalyst $Cr_2O_3$, the yield in fluoral remains low, despite the very high hydrofluoric acid/chloral molar ratio.

French Pat. No. 2,135,474 itself concerns a catalytic process of fluorination in the gaseous phase of perchlorinated compounds into the corresponding perfluorinated compounds according to which the perfluorinated compound involved is obtained in a single passage of the reactants on the catalyst only by conducting the fluorination in three successive reaction zones which are distinct from one another, the temperature of each of the last two reaction zones being controlled at a temperature at least 10° C. higher than that of the temperature of the immediately preceding reaction zone. Such a procedure presumes a complex, delicate and expensive technology. Furthermore, the practical quantity of hydrofluoric acid, which is 1.74 times the stoichiometric molar quantity in the case of fluorination of chloral, renders necessary, for economy of the process, a large recovery and recycling installation for the unconverted hydrofluoric acid.

French Pat. No. 2,135,473 discloses and claims a process adapted to the utilization of a particular catalyst comprising two non-stoichiometric inorganic compounds, one based on chromium and the other on nickel. The use of such a catalyst, not described in this French patent for the fluorination of chloral into fluoral, unfortunately leads to excessive degradation of the organic molecules, due to parasitory cracking reactions, corresponding, in moles, to 7 to 10% of the engaged product to be fluorinated.

The process according to the present invention overcomes the disadvantages of the known processes and allows one to obtain a high and selective transformation of the chloral into fluoral in a single passage of the reactants on the catalyst, in a single reaction zone and with a low hydrofluoric acid/chloral molar ratio.

The process according to the invention is characterized in that the anhydrous hydrofluoric acid and the chloral, in a molar ratio between 3.3:1 and 15:1, preferably between 4:1 and 5:1, react at a temperature between 230° C. and 260° C. on a catalyst comprising a gamma alumina impregnated with chromium sesquioxide $Cr_2O_3$, in a quantity of from 1.5 to 4 and preferably about 2.5 atoms of chromium per liter of alumina, and activated at a temperature between 300° C. and 400° C. by a mixture of hydrofluoric acid and 1,1,2-trichloro-1,2,2-trifluoro-ethane in a molar ratio between about 0.5:1 and 2:1, preferably equal to about 1:1.

In the process according to the invention, impregnation of the alumina is accomplished by known means, such as the simultaneous and separate feeding, under vacuum, into a reactor maintained in rotation and containing the alumina, of a chromic anhydride $CrO_3$ aqueous solution on the one hand, and of methanol, on the other hand, followed by drying the product obtained in a fixed or fluid bed, at a temperature generally close to 150° C. in an inert gas stream such as a nitrogen stream.

Reduction of the hexavalent chromium into trivalent chromium can be carried out by using a reducing compound other than methanol, for example, another alcohol, such as ethanol, or hydrazine. Activation of the catalyst is accomplished, for example, by passage of a mixture of hydrofluoric acid and 1,1,2-trichloro-1,2,2-trifluoro-ethane on the dried catalyst, preferably first at 300° C. or 350° C., thereafter at 400° C.

The absolute pressure at which the fluorination of the chloral is generally carried out is at about 1 bar. The flow-rate of the gaseous reactants on the catalyst is preferably between 150 and 250 1/h/kg of catalyst.

The following examples, given by way of non-limitative illustration, relate to various embodiments of the process according to the invention:

EXAMPLE 1

A $Cr_2O_3$ catalyst on gamma alumina was prepared in the following manner: in a spherical reactor maintained in rotation and under vacuum, containing 0.4 gamma alumina commercialized by the Harshaw company under the reference A1111 73E, the principal characteristics of which are:

presentation: extruded at about 0.8 mm diameter
$SiO_2$ content: 0.13%
total specific surface: 161 m²/g
average pore radius: 105.9 Å
total pore volume: 0.91 ml/g
percentage of pores between 150 and 250 Å: 16.4
percentage of pores between 250 and 300 Å: 1.7 was fed, simultaneously and separately, in about 1 hour, on the one hand, with 190 g. of an aqueous solution containing chromic anhydride $CrO_3$ at a concentration of 52.6% by weight, and on the other hand, with a mixture of methanol and water containing 80% by weight methanol, the alumina thus impregnated being thereafter dried in a fluid bed at 150° C. in a nitrogen stream. A quantity of 0.189 kg of dry catalyst was activated in a tubular fluorination reactor of 40 mm diameter, first at 350° C. for six hours and then at 400° C. for 24 hours, by passage of 13.5 Nl/h of an equimolecular gaseous mixture of hydrofluoric acid and 1,1,2-trichloro-1,2,2-trifluoro-ethane. On the catalyst thus activated and in the reactor having been used for the activation but heated to 250° C. and under an absolute pressure of 1 bar were thereafter passed at 38 1/h of a gaseous mixture containing anhydrous hydrofluoric acid and chloral in a molar ratio equal to 4.25:1.

Analysis of the gaseous effluent from the reactor showed that the overall rate of fluorination with respect to hydrofluoric acid, i.e. the ratio of the number of HF moles consumed to the number of HF moles corresponding to the stoichiometry of the transformation reaction of the chloral into fluoral, was 98%; that the conversion of the chloral into fluoral was 95.1%; that the selectivity to fluoral, expressed as being the percentage of fluoral moles formed with respect to the moles of fluorinated derivative of acetaldehyde formed, chlorinated or not, was 98.2%; and that, furthermore, the productivity reached 0.156 kg of fluoral/h/kg of catalyst and the chloral rate in the degraded form following the parasite reactions was lower than 2%.

EXAMPLE 2

Operating according to Example 1 but with a HF/chloral molar ratio of 4.5:1, the overall rate of fluorination with respect to HF was 100%, the conversion of the chloral into fluoral was 96.5%, the fluoral selectivity was 98.5% and the yield was 0.160 kg of fluoral/h/kg of catalyst, and the degradation rate of the chloral remained lower than 2%.

Similar results were obtained by carrying out the activation of the dried catalyst in a tubular reactor of 28 mm diameter, first at 350° C. for 2 hours and then at 400° C. for 22 hours, by passage of 31.2 Nl/h of hydrofluoric acid and 14.3 Nl/h of 1,1,2-trichloro-1,2,2-trifluoro-ethane.

EXAMPLE 3

Operating according to Example 1 but with a HF/chloral molar ratio of 4.7:1, the overall fluorination rate with respect to HF was 100%, the conversion of the chloral into fluoral was 98.5%, the fluoral selectivity was 98% and the yield was 0.158 kg fluoral/h/kg of catalyst, the degradation rate of the chloral not exceeding 2%.

EXAMPLE 4

The test corresponding to this example, carried out by operating as in Examples 1 to 3 but with a HF/chloral molar ratio of 6.3:1, led to results that were substantially identical to those indicated in those examples and confirmed that the process of the invention presents the supplementary advantage of achieving results substantially insensitive to the HF excess with respect to the stoichiometry of the transformation reaction of the chloral into fluoral when this excess varies from 30% to about 100%.

EXAMPLE 5

Operating according to Example 1 but at a temperature of 235° C., the overall fluorination rate with respect to HF was 77.9%, the conversion of the chloral into fluoral reached 71.6%, the yield was 0.12 kg fluoral/h/kg of catalyst, the degradation rate of the chloral being lower than 0.5%.

EXAMPLE 6

Operating according to Example 1 but with a HF/chloral molar ratio of 10.3, the overall fluorination rate with respect to HF was 100%, the conversion of the chloral into fluoral was 95.4%, the fluoral selectivity was 97.8% and the yield was 0.082 kg fluoral/h/kg of catalyst, the degradation rate of the chloral being about 2.5%.

EXAMPLE 7

An amount of 0.223 kg of dry catalyst according to Example 1 was activated in a tubular reactor of 28 mm diameter, first at 350° C. for 16 hours and then at 400° C. for 8 hours, by passage of 7.7 Nl/h of hydrofluoric acid and 6.2 Nl/h of 1,1,2-trichloro-1,2,2-trifluoro-ethane (molar ratio: 1.24). The catalyst thus activated was used to fluorinate chloral in the same reactor as in Example 1 and under the same conditions with the exception that the molar ratio HF/chloral was 4.3. After 96 hours of operation, the catalyst was regenerated by passage of an air and chlorine mixture at 400° C. for 3 hours. Then, the fluorination operation was resumed. After one hour, the overall fluorination rate with respect to HF was 100%, the conversion of the chloral into fluoral was 92.7%, the fluoral selectivity was 98.3% and the productivity reached 0.129 kg of fluoral/h/kg of catalyst, the degradation rate of the chloral being about 5.7%.

What is claimed is:

1. A continuous catalytic process for the preparation of trifluoroacetaldehyde through fluorination of trichloroacetaldehyde in the gaseous phase by anhydrous hydrofluoric acid in a single reaction zone, which comprises reacting the hydrofluoric acid and the trichloroacetaldehyde, in a molar ratio between 3.3:1 and 15:1, at a temperature between 230° C. and 260° C., and on a catalyst comprising a gamma alumina impregnated with chromium sesquioxide $Cr_2O_3$ in an amount of from 1.5 to 4 atoms of chromium per liter of alumina and activated at a temperature between 300° C. and 400° C. by means of a mixture of hydrofluoric acid and 1,1,2-trichloro-1,2,2-trifluoro-ethane in a molar ratio between about 0.5:1 and 2:1.

2. The process according to claim 1, wherein the flow-rate of the reactants on the catalyst is between 150 and 250 l/h/kg of catalyst.

3. The process according to claim 2, in which the molar ratio of hydrofluoric acid to trichloroacetaldehyde is between 4:1 and 5:1.

4. The process according to claim 1, in which the molar ratio of hydrofluoric acid to trichloroacetaldehyde is between 4:1 and 5:1.

5. The process according to claim 4, in which the catalyst contains about 2.5 atoms of chromium per liter of alumina and is activated by means of substantially equimolar mixture of hydrofluoric acid and 1,1,2-trichloro-1,2,2-trifluoroethane.

6. The process according to claim 3, in which the catalyst contains about 2.5 atoms of chromiun per liter of alumina and is activated by means of substantially equimolar mixture of hydrofluoric acid and 1,1,2-trichloro-1,2,2-trifluoroethane.

7. The process according to claim 2, in which the catalyst contains about 2.5 atoms of chromium per liter of alumina and is activated by means of substantially equimolar mixture of hydrofluoric acid and 1,1,2-trichloro-1,2,2-trifluoroethane.

8. The process according to claim 1, in which the catalyst contains about 2.5 atoms of chromium per liter of alumina and is activated by means of substantially equimolar mixture of hydrofluoric acid and 1,1,2-trichloro-1,2,2-trifluoroethane.

* * * * *